United States Patent
Griswold et al.

(10) Patent No.: US 10,500,585 B2
(45) Date of Patent: Dec. 10, 2019

(54) EXTRACTION OF RESTRAINED LIQUID FROM WELLS

(71) Applicant: Takara Bio USA, Inc., Mountain View, CA (US)

(72) Inventors: Bradley L. Griswold, Fremont, CA (US); Syed A. Husain, Fremont, CA (US); Robert Moti, Fremont, CA (US); Wesley B. Dong, Fremont, CA (US); GoPaul Kotturi, Fremont, CA (US); Jude Dunne, Fremont, CA (US); Philip Lin, Fremont, CA (US)

(73) Assignee: TAKARA BIO USA, INC., Mountain View, CA (US)

( * ) Notice: Subject to any disclaimer, the term of this patent is extended or adjusted under 35 U.S.C. 154(b) by 24 days.

(21) Appl. No.: 15/269,258

(22) Filed: Sep. 19, 2016

(65) Prior Publication Data
US 2017/0001193 A1    Jan. 5, 2017

Related U.S. Application Data

(63) Continuation of application No. 14/075,631, filed on Nov. 8, 2013, now Pat. No. 9,447,925.
(Continued)

(51) Int. Cl.
*B01L 3/00* (2006.01)
*F17D 1/08* (2006.01)
(Continued)

(52) U.S. Cl.
CPC ......... *B01L 3/5025* (2013.01); *C12Q 1/6806* (2013.01); *F17D 1/08* (2013.01);
(Continued)

(58) Field of Classification Search
CPC ............... B01L 3/00; B01L 2300/0829; B01L 2300/0819; B01L 2200/025; C12M 1/00
(Continued)

(56) References Cited

U.S. PATENT DOCUMENTS 4,902,481 A * 2/1990 Clark .................... B01D 61/18
                                                      210/335
6,083,761 A    7/2000 Kedar et al.
(Continued)

FOREIGN PATENT DOCUMENTS

| WO | 99/51349 | 10/1999 |
| WO | 03/028878 | 4/2003 |
| WO | 2009/129397 | 10/2009 |

OTHER PUBLICATIONS

Methods Mol. Biol. vol. 20 (1993), Only Table of Contents provided, will provide specific passages upon Examiner request.
(Continued)

*Primary Examiner* — Natalia Levkovich
(74) *Attorney, Agent, or Firm* — Michael J. Blessent; Bret E. Field; Bozicevic, Field & Francis LLP (57) ABSTRACT

The present invention provides methods, systems, assemblies, and articles for extracting restrained liquid (e.g., surface tension-restrained liquid) from open wells in a chip, where the restrained liquid does not flow out of the wells due to gravity when the wells are held upside down. For example, the present invention provides extraction fixtures that may be attached to, and/or held adjacent to, a chip such that any restrained liquid that is forced out of the open wells is collected by, or flows through, the extraction fixtures. Also for example, the present invention provides assemblies composed of a extraction fixture attached to, and/or held adjacent to, a chip, and methods of subjecting such assemblies to a force such that at least a portion of the restrained
(Continued)

Section B-B liquid in the open wells is forced out and collected by, or flows through, the extraction fixture.

15 Claims, 5 Drawing Sheets

Related U.S. Application Data (60) Provisional application No. 61/724,118, filed on Nov. 8, 2012, provisional application No. 61/777,459, filed on Mar. 12, 2013.

(51) Int. Cl.
*C12Q 1/6806* (2018.01)
*G01N 1/28* (2006.01)

(52) U.S. Cl.
CPC ........ *G01N 1/28* (2013.01); *B01L 2300/0609* (2013.01); *B01L 2300/0819* (2013.01); *B01L 2300/0893* (2013.01); *B01L 2300/0896* (2013.01); *B01L 2300/126* (2013.01); *B01L 2400/0409* (2013.01); *Y10T 137/0391* (2015.04); *Y10T 137/8593* (2015.04); *Y10T 436/2575* (2015.01)

(58) Field of Classification Search
USPC .......................................... 422/552, 553, 503
See application file for complete search history.

(56) References Cited

U.S. PATENT DOCUMENTS

| | | | |
|---|---|---|---|
| 6,833,112 B2 * | 12/2004 | Hoummady | ......... B01J 19/0046 347/21 |
| 7,547,556 B2 | 6/2009 | Hunter et al. | |
| 7,833,709 B2 | 11/2010 | Joseph et al. | |
| 8,252,581 B2 | 8/2012 | Joseph et al. | |
| 9,447,925 B2 | 9/2016 | Griswold et al. | |
| 2002/0164820 A1 | 11/2002 | Brown | |
| 2005/0167899 A1 | 8/2005 | Aldridge et al. | |
| 2008/0199851 A1 | 8/2008 | Egan et al. | |
| 2010/0252128 A1 | 10/2010 | Gong et al. | |
| 2011/0065591 A1 | 3/2011 | Takagi | |
| 2012/0108461 A1 | 5/2012 | Bussan et al. | |
| 2015/0209786 A1 * | 7/2015 | Hage | .................... B01L 3/5025 435/6.12 |

OTHER PUBLICATIONS

Beier et al., "Versatile Derivatisation of Solid Support Media for Covalent Bonding on DNA-microchips," Nucleic Acids Research, 1999, 27(9):1970-1-977.

Joos et al., "Covalent attachment of hybridizable oligonucleotides to glass supports," Analytical Biochemistry, 1997, 247(1):96-101.

Guschin et al., "Manual Manufacturing of Oligonucleotide, DNA, and Protein Microchips," Analytical Biochem., 1997, 250:203-211.

Rahman, L. (Senior Paper Scientist) "Factors Affecting the Performance of Inkjet Papers," TAPPI Spring Technical Conference & Trade Fair, 2003.

Du et al., "Automated Microfluidic Screening Assay Platform Based on DropLab," Analytical Chemistry, 2010, 82:9941-9947.

International Search Report and Written Opinion for PCT/US2013/06914, dated May 22, 2014, 13 pages.

Extended European Search Report for EP Patent Application 13852704.9, dated Jun. 1, 2016, 6 pages.

Leamon et al., A massively parallel PicoTiterPlate based platform for discrete picoliter-scale polymerase chain reactions. Electrophoresis. Nov. 2003;24(21):3769-77.

* cited by examiner

FIG. 4

EXTRACTION OF RESTRAINED LIQUID FROM WELLS

The present application is a continuation of U.S. patent application Ser. No. 14/075,631, filed Nov. 8, 2013, which claims priority to U.S. Provisional Application 61/724,118 filed Nov. 8, 2012 and U.S. Provisional Application 61/777,459 filed Mar. 12, 2013, each of which are herein incorporated by reference.

FIELD OF THE INVENTION

The present invention provides methods, systems, assemblies, and articles for extracting restrained liquid (e.g., surface tension-restrained liquid) from open wells in a chip. For example, the present invention provides extraction fixtures that may be attached to, and/or adjacent to, a chip such that any restrained liquid that is forced out of the open wells is collected by, or flows through, the extraction fixtures.

BACKGROUND

A typical nanowell chip is composed of a 72×72 array (5184) of wells or cavities in the chip substrate. In such typical chips, each well is 450 μm in diameter and 940 μm deep and is filled with nanoliter volumes of liquid reactant. The small size precludes removal of the reacted material by pipette, for example, as is done with conventional 96 or 384 well plates. Given the small size of the wells, the surface tension of the fluid inside the wells becomes a much larger component of the forces that must be overcome to remove the liquid from the wells, thus complicating the removal process.

SUMMARY OF THE INVENTION

The present invention provides methods, systems, assemblies, and articles for extracting restrained liquid (e.g., surface tension-restrained liquid) from open wells (e.g., nanowells) in a chip, where the surface tension-restrained liquid does not flow out of the wells due to gravity when the wells are held upside down. For example, the present invention provides extraction fixtures that may be attached to, and/or adjacent to, a chip such that any restrained liquid (e.g., surface tension-restrained liquid) that is forced out of the open wells is collected by, and/or flows through, the extraction fixtures. Also for example, the present invention provides assemblies composed of an extraction fixture attached to, and/or adjacent to, a chip, and methods of subjecting such assemblies to a force such that at least a portion of the restrained liquid in the open wells is forced out and collected by, and/or flows through, the extraction fixture. In certain embodiments, where the liquid flows through the extraction fixture, it is collected in a collection tube.

In some embodiments, the present invention provides methods of removing restrained liquid (e.g., surface tension-restrained liquid) from at least one open well in a chip comprising: a) providing an assembly comprising at least one extraction fixture adjacent to, and/or attached to, a chip, i) wherein the chip comprises a substrate and a plurality of open wells (or at least one open well) formed in the substrate, wherein the plurality of open wells contain restrained liquid, and ii) wherein the at least one extraction fixture is adjacent to, and/or attached to, the chip such that any of the restrained liquid that is forced out of the plurality of open wells is collected by the at least one extraction fixture; and b) subjecting the assembly to a force such that at least a portion of the restrained liquid becomes released liquid that flows out of at least one of the plurality of open wells and is held by, or flows through (e.g., into a collection tube), the at least one extraction fixture. In certain embodiments, the extraction fixture is composed of multiple components that enclose the chip.

In certain embodiments, the present invention provides methods of removing restrained liquid (e.g., surface tension-restrained liquid) from at least one open well in a chip comprising: subjecting an assembly to a force, wherein the assembly comprises at least one extraction fixture adjacent to, and/or attached to, a chip, wherein the chip comprises a substrate and a plurality of open wells (or at least one open well) formed in the substrate, wherein the plurality of open wells contain restrained liquid, and wherein the subjecting the assembly to a force causes at least a portion of the restrained liquid to become released liquid that flows out of at least one of the plurality of open wells where it is held by, or flows through, the at least one extraction fixture.

In particular embodiments, the force is selected from the group consisting of centripetal force, centrifugal force, vacuum force, and sudden deceleration (e.g., stop of motion), or any other dislodging force. In other embodiments, the force is generated by a centrifuge or similar device.

In further embodiments, the present invention provides an assembly comprising: at least one extraction fixture adjacent to, and/or attached to, a chip, wherein the chip comprises a substrate and a plurality of open wells (or at least one open well) formed in the substrate, wherein the plurality of open wells contain liquid and are dimensioned such that surface tension or other restraining force prevents the liquid from flowing out of the open wells regardless of orientation of the chip, and wherein the at least one extraction fixture is attached to, and/or adjacent, to the chip such that any of the liquid that is forced out of the plurality of open wells is collected by, or flows through (e.g., into a collection tube), the at least one extraction fixture.

In some embodiments, the present invention provides systems comprising: a) a chip, wherein the chip comprises a substrate and a plurality of open wells (or at least one open well) formed in the substrate, wherein the plurality of open wells contain restrained liquid, and b) at least one extraction fixture dimensioned to be attached to, and/or held adjacent to, the chip to form an assembly, and wherein the at least one extraction fixture is further dimensioned such that when the restrained liquid is present in the plurality of open wells and is forced out of the plurality of open wells to form released liquid, the released liquid is collected by, or flows through (e.g., into a collection tube), the at least one extraction fixture. In further embodiments, the systems further comprise c) a device configured to apply a force to the assembly. In particular embodiments, the device comprises a centrifuge.

In certain embodiments, the present invention provides an article of manufacture comprising: a extraction fixture dimensioned to be attached to a chip to form an assembly (and/or dimensioned to be held adjacent to a chip), wherein the chip comprises a substrate and a plurality of open wells (or at least one open well) formed in the substrate, wherein the plurality of open wells contain restrained liquid, and wherein the extraction fixture is further dimensioned such that when restrained liquid is present in the plurality of open wells and is forced out of the plurality of open wells to become released liquid, at least part of the released liquid is collected by, or flows through, the extraction fixture.

In some embodiments, the present invention provides methods of making an assembly comprising: a) attaching at least one extraction fixture to a chip (or holding an extraction fixture adjacent to a chip) to form an assembly, wherein the chip comprises a substrate and a plurality of open wells (or at least one open well) formed in the substrate, wherein the plurality of open wells contain restrained liquid, wherein the at least one extraction fixture is attached to (and/or adjacent to) the chip such that any of the restrained liquid that is forced out of the plurality of open wells to become released liquid is collected by, or flows through, the at least one extraction fixture, and b) sealing the at least one extraction fixture to the chip with a sealing component such that a water tight seal between at least a portion of the chip and the at least one extraction fixture is formed. In certain embodiments, the sealing component comprises an O-ring or other gasket. In other embodiments, the sealing component is selected from the group consisting of: screws, adhesive, at least one clamp, and bolts.

In particular embodiments, the present invention provides methods comprising: a) providing a chip, wherein the chip comprises a substrate and a plurality of open wells (or at least one open well) formed in the substrate, wherein the plurality of open wells contain restrained liquid, and wherein the chip is at least partially covered with a sealing film which covers the plurality of open wells; b) removing at least a portion of the sealing film from the chip to create an open area; c) attaching an extraction fixture to the chip (or holding the extraction fixture adjacent to the chip) such that the open area is covered by the extraction fixture to form an assembly, wherein the extraction fixture is attached to, and/or adjacent to, the chip such that any of the restrained liquid that is forced out of the plurality of open wells to become released liquid is held by, or flows through, the extraction fixture; and d) sealing the at least one extraction fixture to the chip with a sealing component such that a water tight seal between at least a portion of the chip and the extraction fixture is formed. In certain embodiments, the methods further comprise step e) subjecting the assembly to a force such that at least a portion of the surface tension-restrained liquid flows out of at least one of the plurality of open wells to become released liquid that is collected by, or flows through, the extraction fixture.

In particular embodiments, the at least one extraction fixture comprises an extraction fixture base, wherein said extraction fixture base comprises a conical section dimensioned to collect fluid. In other embodiments, the at least one extraction fixture comprises an extraction fixture base, wherein the extraction fixture base comprises at least one of the following: i) a pocket component dimensioned to hold the chip, ii) a conical section dimensioned to collect fluid, and iii) a gasket track dimensioned to hold a gasket. In further embodiments, the at least one extraction fixture further comprises an extraction fixture top plate dimensioned to attach to the extraction fixture base (e.g., such that said chip is enclosed therein). In certain embodiments, the at least one extraction fixture further comprises: i) an extraction fixture top plate dimensioned to attach to the extraction fixture base, ii) a paper gasket configured to fit between the chip and the extraction fixture top plate, and/or iii) a sample cup configured to allow a sample to be dispensed through the fixture top plate. In further embodiments, the conical section comprises a fluid holding component dimensioned to allow a pipette to remove any of the released liquid located therein. In some embodiments, the liquid that flows out of at least one of the plurality of open wells is held by said at least one extraction fixture.

In particular embodiments, the assemblies, systems, and methods further have a base holding component, wherein the base holding component is dimensioned to hold the at least one extraction fixture adjacent to the chip. In some embodiments, the assemblies, systems, and methods further comprise at least one collection tube mounted in the base holding component, wherein the liquid flows out of at least one of the plurality of open wells flows through the at least one extraction fixture into the at least one collection tube. In other embodiments, the base holding component is dimensioned to hold at least two of the extraction fixtures adjacent to said chip (e.g., at least 2, 3, 4, 5, 6, 7, 8, 9, 10 or more extraction fixtures). In additional embodiments, the at least one extraction fixture is attached to said chip. In particular embodiments, the base holding component is dimensioned to hold at least one extraction fixture adjacent to a chip (e.g., on one end) and adjacent to a collection tube (e.g., on the other end). In certain embodiments, the collection tube comprises a polymerase chain reaction tube, EPPENDORF, or similar type tubes.

In other embodiments, the at least one extraction fixture comprises: i) a cover component, and ii) a fluid holding component; wherein the cover component is dimensioned to cover at least a portion of the chip and comprises a port releasably attached to the fluid holding component. In particular embodiments, the fluid holding component comprises a test tube. In some embodiments, the cover component has a generally planar shape in the area around the port.

In certain embodiments, at least 25% (e.g., 25% . . . 35% . . . 50% . . . 60% . . . 75% . . . 85% . . . 95% . . . 98% . . . 99.5% . . . 99.9% . . . 100%) of the restrained liquid (e.g., surface tension-restrained liquid) becomes released liquid and flows out of the plurality of open wells and is held by, or flows through, the extraction fixture. In some embodiments, the at least one extraction fixture comprises at least two extraction fixtures (e.g., 2, 3, 4, 5, 6, 7, 8, 9, 10, 11, 12, 13, 14, 15 . . . 25 or more). In particular embodiments, at least some of the plurality of open wells has a volume between 0.1 nanoliters and 500 nanoliters (e.g., about 0.1 nl . . . 0.9 nl . . . 1.5 nl . . . 5.0 nl . . . 10 nl 20 nl . . . 35 nl . . . 50 nl . . . 75 nl . . . 100 nl . . . 150 nl . . . 300 nl . . . 450 nl . . . 500 nl). In particular embodiments, at least some of the plurality of open wells has a volume between 1.0 nanoliter and 250 nanoliters (e.g., 1-250 nl, 10-200 nl, 25-150 nl, 40-100 nl, or 50-100 nl).

In some embodiments, the plurality of open wells comprises at least 3 open wells (e.g., 3 . . . 10 . . . 100 . . . 350 . . . 500 . . . 750 . . . 1000 . . . 1500 . . . 3000 . . . 5000 . . . 7500 . . . 10,000 . . . 15,000 . . . 20,000 . . . 30,000 . . . 45,000 or more open wells). In other embodiments, the restrained liquid comprises PCR reagents (e.g., primers, polymerase, water, buffer, template nucleic acid sequence, reverse transcriptase, etc.). In other embodiments, the restrained liquid comprises amplified nucleic acid. In further embodiments, the methods further comprise a step of subjecting the released liquid that is held by, or flows through, the at least one extraction fixture to a nucleic acid detection assay.

In additional embodiments, the chip has a length of 10 mm to 200 mm (e.g., 10 mm 50 mm . . . 100 mm 150 mm . . . or 200 mm), a width of 10 mm to 200 mm (e.g., 10 mm 50 mm . . . 100 mm 150 mm . . . or 200 mm), and a thickness of 0.1 mm to 10 centimeters (e.g., 0.1 mm . . . 1.0 mm 10 mm . . . 10 cm). In other embodiments, the substrate comprises a material selected from the group consisting of: glass, ceramics, metalloids, silicon, a silicate, silicon nitride, silicon dioxide, quartz, gallium arsenide, a plastic, and an organic polymeric material. In additional embodiments, the chip further comprises individually-controlled heating elements, each of which is operably coupled to an open well. In some embodiments, the at least one extraction fixture is attached to the chip by an attachment component selected from the group consisting of: screws, adhesive, at least one clamp, and bolts.

In some embodiments, the present invention provides methods for decreasing the dynamic range of amplicon production on a nanowell chip comprising: i) identifying at least one well in a initial nanowell chip that produces increased or decreased amplicon production from a particular target during amplification relative to the average amplicon production during amplification of all the wells in said nanowell chip; and ii) performing amplification using a test nanowell chip set up identical to said initial nanowell chip except for at least of the following: A) additional wells on said test nanowell chip are employed for targets identified as having decreased amplicon production; B) targets found to have increased expression are combined with other targets such that multiplex amplification occurs in a single well; C) increasing the primer concentration in a well found to have low amplicon production; D) decreasing primer concentration in a well found to have high amplicon production; E) including inhibitors in wells found to have high amplicon production; F) switching to less efficient primers in wells found to have high amplicon production; G) altering the thermalcycling temperature and/or times in a well to increase amplicon production if amplicon production is decreased or to decrease amplicon production if amplicon production is increased; and H) altering the depth, width, and/or volume of a well to increase amplicon production if amplicon production is decreased or to decrease amplicon production if amplicon production is increased.

Definitions

As used here, liquid is "restrained" in an open well of a chip when the liquid does not flow out of the well due to gravity when the chip is held upside down such that the opening of the well is facing the ground. In certain embodiments, the liquid is restrained in a well due to surface-tension (i.e., the liquid is surface tension-restrained liquid).

DESCRIPTION OF THE FIGURES

FIG. 3 shows the paper gasket (70) between the nanowell chip (10) and the fixture top plate (30). Also shown in FIG. 3 is a sample cup (90) in fixture top plate (30) where sample can be introduced. A protective label (45) is shown which can cover the sample cup (90). Four screws (40) are shown in fixture top plate (30) for attaching all of the components together (e.g., for anchoring in the holes shown in extraction fixture base (20)). Also shown in extraction fixture base (20) is gasket track (28) shown with a rubber gasket in place.

FIG. 4 shows various exemplary embodiments of bulk fill fixtures in the fixture top plates. Figure A-1 shows a top view of a fixture top plate (30) with a sample cup (90) formed in the center thereof with a septum (80) in the center of the sample cup (90) to allow needle injection of sample into the sample cup (e.g., needle injection of target sample when the extraction fixture is on top of a vacuum fill station that draws the sample down into the nanowell chip below). Figure A-2 shows a side view of the sample cup (90) through section A-A of Figure A-1. Figure B-1 shows a top view of a fixture top plate (30) with a sample cup (90) formed in the center thereof, while Figure B-2 shows a side view of Figure B-1 through section B-B. Figure B-3 shows a blow up of the bulk fill fixture in Figure B-2, showing a spigot (110) and a duckbill valve (101) on top of the spigot, which allows air out when a vacuum is applied (or released) drawing the sample down (part 120 shows an exemplary liquid front and how the liquid can flow onto the chip when a vacuum is released, or applied) into the nanowell chip (10) thereby preventing bubbling of liquid in the sample cup. Figure C-1 shows a top view of a fixture plate (30) with a sample cup (90) formed in the center thereof, while Figure C-2 shows a side view of Figure C-1 through section C-C. Figure C-3 shows a blow up of the bulk fill fixture in Figure C-2, showing a spigot (110) and a combo valve (102) which vents through a duckbill valve while allowing liquid to flow in thru the umbrella portion.

DETAILED DESCRIPTION

The present invention provides methods, systems, assemblies, and articles for extracting restrained liquid from open wells in a chip, where the liquid does not flow out of the wells due to gravity when the wells are held upside down. For example, the present invention provides extraction fixtures that may be attached to a chip such that any restrained liquid that is forced out of the open wells is collected by, for flow through, the extraction fixtures. Also for example, the present invention provides assemblies composed of an extraction fixture attached to a chip, and methods of subjecting such assemblies to a force such that at least a portion of the restrained liquid in the open wells is forced out and is held by, or flows through, the extraction fixture.

In certain embodiments, the present invention allows restrained liquid in wells (e.g., nanowells) in a chip to be released and combined in to a single pool (e.g., all of the liquid from a particular chip is combined into a single liquid sample). In some embodiments, the present invention employs a centrifuge or similar device to provide the force necessary to extract the restrained reactant liquid from a nanowell chip.

In work conducted during the development of embodiments of the present invention, the feasibility of this nanowell extraction concept was tested using a simple extraction fixture that was taped to a SMARTCHIP nanowell chip from Wafergen, Fremont, Calif. The concept was tested by weighing a nanowell chip before and after filling to determine the exact amount of reactant in the wells. The extraction fixture was taped onto the chip and the whole thing placed into the arm of a centrifuge such that the centripetal force would act to push the fluid out of the wells. Two assemblies were used to keep the centrifuge balanced by loading them on opposing sides. The extraction fixture was also weighed before spinning the chip/fixture combination. The test was run in the centrifuge for 15 minutes at 2000 rpm. The extraction fixture was removed and weighed. Approximately 15% of the fluid that was originally in the chip was captured in the extraction fixture.

Figure 1:
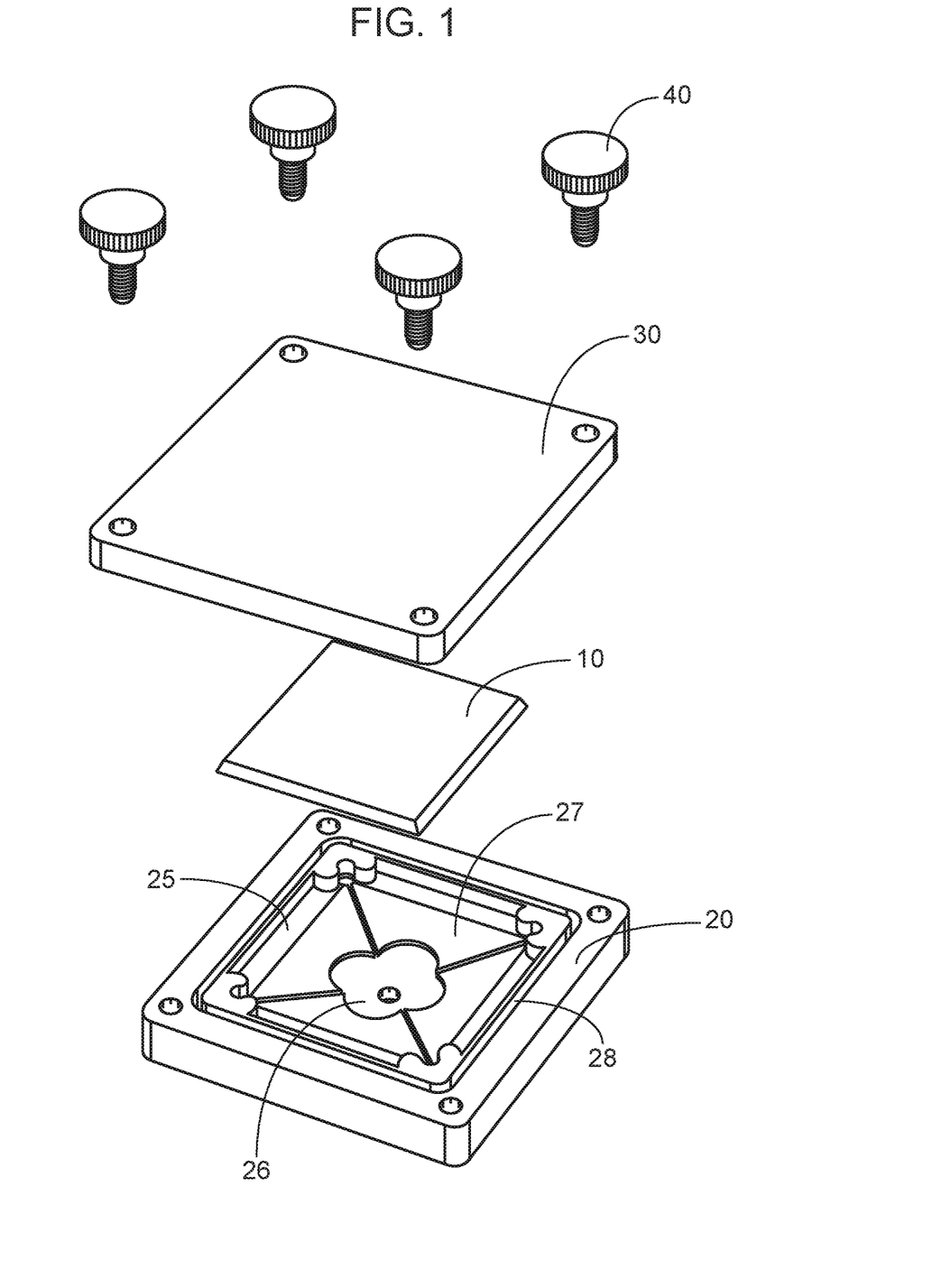
FIG. 1 shows a nanowell chip (10) that can be positioned within an extraction fixture composed of an extraction fixture base (20) and an extraction fixture top plate (30) which are attached to each other by four thumb screws (40). The extraction fixture base (20) shown in this exemplary embodiment has: a pocket component (25) for holding the chip, a conical section (27) for collecting fluid and which comprises a fluid holding component (26), and a gasket track (28) for holding a gasket (e.g., O-ring) that helps form a liquid tight seal between the extraction fixture top plate (30) and the extraction fixture base (20).

In other work conducted during the development of the present invention, using the components in FIG. 1, the chip (SMARTCHIP) to be extracted was placed well side down so that it faced the conical section of the extraction fixture. The chip rested in a pocket above the conical section and the top section of the extraction fixture then locked the chip into place when it is tightened down with the four thumb screws. The whole extraction fixture is sealed by an O-ring keeping the extracted fluid contained until it is removed for further analysis. Note that the conical section is divided into two parts, the large cone which captures the fluid during centrifuging and the smaller section which concentrates the captured fluid into a smaller area. This allows the extracted fluid to be removed by pipette for transfer into another container. The extraction fixture is then placed into a common laboratory centrifuge and spun. Testing has shown that the speed of the centrifuge is important to recovering a greater percentage of liquid. If the rotation is below a certain speed (e.g., depending on the size of the nanowells in the chip), little to no fluid is removed from the nanowell chip. This is because the force generated by the centrifuge is not sufficient to overcome the surface tension forces holding the fluid in the well. Above a particular speed (e.g., for a particular size of nanowell), the extraction can be efficient, capturing over 75% of the fluid originally in the nanowell chip. In certain embodiments, the assembly should be spun above 2000 rpm to achieve 75% extraction.

In certain embodiments, the extraction fixtures are used to collect multiple samples (e.g., pooled samples) from a single chip (e.g., multiple extraction fixtures are used on a single chip). An example of such embodiments is as follows. In this embodiment, the chip is divided geographically into discrete sections, such as 4 or 9 sections. Each section is separated from the adjacent one by a sealing "street" which is formed by milling surfaces approximately 4 mm wide. The chip may be loaded with the reagents (e.g., PCR reactants) by a multisample nanodispenser and treated to reaction conditions (e.g., heating and cooling cycles for PCR reaction). After thermocycling, the sealing film is excised one section at a time by running a razor blade or other cutting component on the cutting line which is present at the center of each sealing "street." In particular embodiments, only one section is excised at any one time and an individual extraction fixture is placed over the section and sealed by a PSA (pressure sensitive adhesive) on its bottom edge. In such embodiments, the arrangement described in FIG. 2 may be employed. Each of the individual extraction fixtures may have a port which will accept, for example, a 200 ul collection tube. The subsequent sections may be de-filmed and covered in the same manner. Once all the individual extraction fixtures are in place, in certain embodiments, a clamp is attached that clamps down the individual extraction fixtures simultaneously. In other embodiments, not clamp is employed. The entire assembly is then placed in a centrifuge and processed as described in the single sample embodiment above. Once the centrifuge step is completed, the chip assembly is removed and positioned on a fixture with the chip side up. In this orientation, the contents of the nanowells is pooled at the bottom of the collection tube. The individual collection tubes may be removed and capped followed by installing an empty tube in its place before removing the next tube to prevent any contamination (e.g., of amplicons in the liquid). Once the user has removed and capped the chip assembly with empty collection tubes, the entire assembly can be discarded. Such embodiments allow the amplification or other manipulation of individual samples without the risk of cross contamination of amplicons from the different sections. Another method of sample extraction is through the use of a septum seal on the side of a the base holding component and then using a hypodermic syringe to extract the centrifuged contents.

In certain embodiments, the extraction fixtures are configured to collect all of the liquid from a nanowell chip into a single pool. An exemplary embodiment is shown in FIG. 1, where the extraction fixture is composed of an extraction base (20) and an extraction fixture top plate (30) that mate and surround a chip. The extraction fixture top plate (30) and extraction fixture base (20) can be attached to each other with any type of component (e.g., screws, adhesive, VELCRO, etc.). In FIG. 1, the attachment component are four thumb screws (40). The extraction fixture base (20), as shown in FIG. 1, may have: a pocket component (25) for holding the chip, a conical section (27) for collecting fluid (which may comprise a fluid holding component (26)), and a gasket track (28) for holding a gasket (e.g., O-ring) that helps form a liquid tight seal between the extraction fixture top plate (30) and the extraction fixture base (20).

Figure 2A:
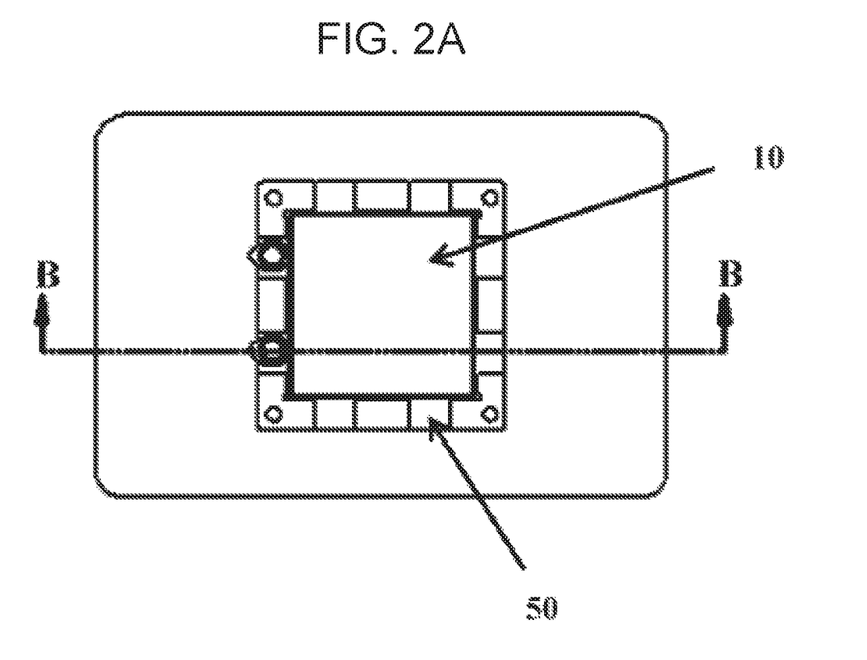
FIG. 2A shows a top-down view of a base holding component (50) with a nanowell chip (10) situated on top.
Figure 2B:
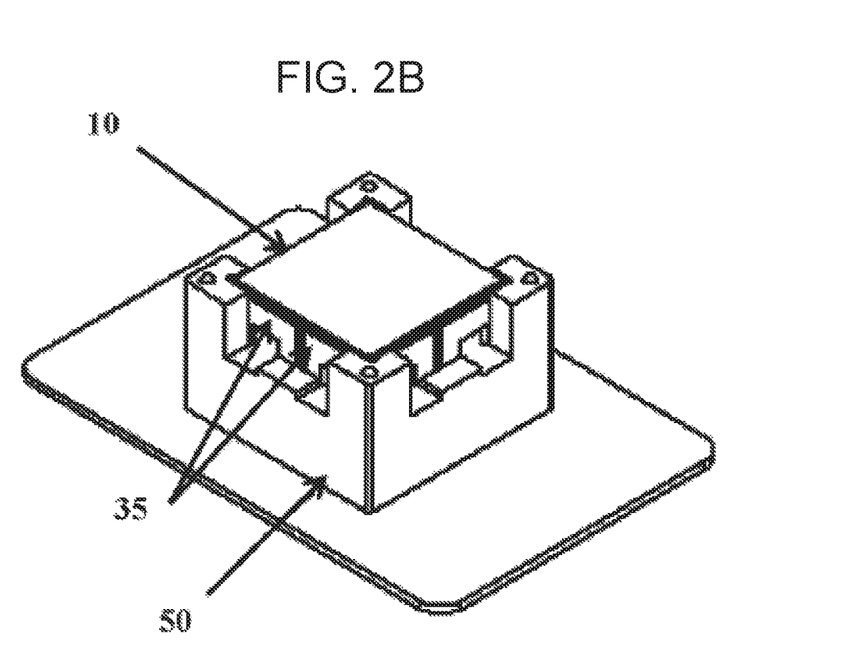
FIG. 2B shows a side perspective view of a base holding component (50) with four extraction fixtures (35) held in the base holding component (50) below, and adjacent to, a nanowell chip (10).
Figure 2C:
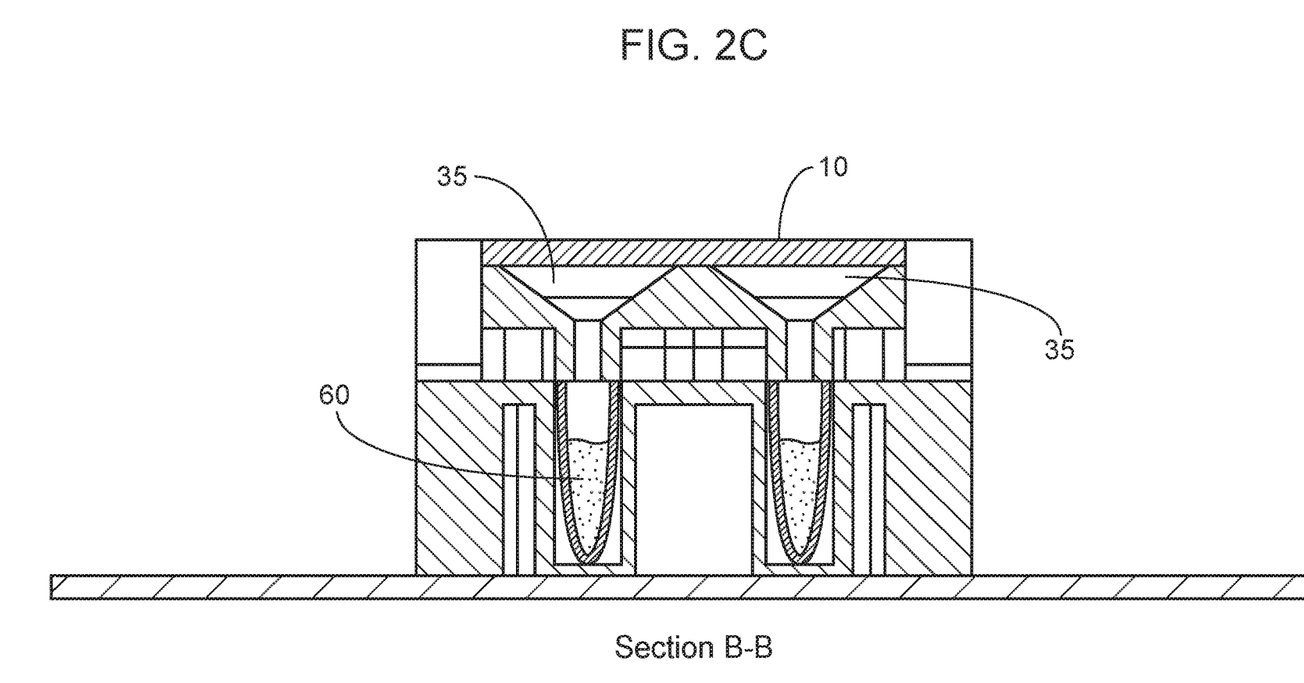
FIG. 2C shows a cross section of the base holding component (50) through section B-B from FIG. 2A. The cross section in FIG. 2C shows two of the four extraction fixtures (35) that are held within the base holding component (50) above the collection tubes (60).

In some embodiments, multiple extraction fixtures are used together, such that each extraction fixture collects a portion of the liquid of the wells of a chip. An exemplary embodiment is shown in FIG. 2, where four extraction fixtures, held inside a base holding component, are used. In FIG. 2A, a base holding component (50) is shown with an upside down nanowell chip (10) situated on top. FIG. 2B shows a side perspective view of a base holding component (50) with four extraction fixtures (35) held in the base holding component (50) below, and adjacent to, a nanowell chip (10). Other numbers of extraction figures can be used in a base holding component, such as 1, 2, 3, 5, 6, 7, 8, 9, or more. FIG. 2C shows a cross section of the base holding component (50) through section B-B from FIG. 2A. The cross section in FIG. 2C shows two of the four extraction fixtures (35) that are held within the base holding component (50) above the collection tubes (60). The collection tubes may be PCR tubes (e.g., 200 µl) or any other type of suitable tube or collection container.

Figure 3:
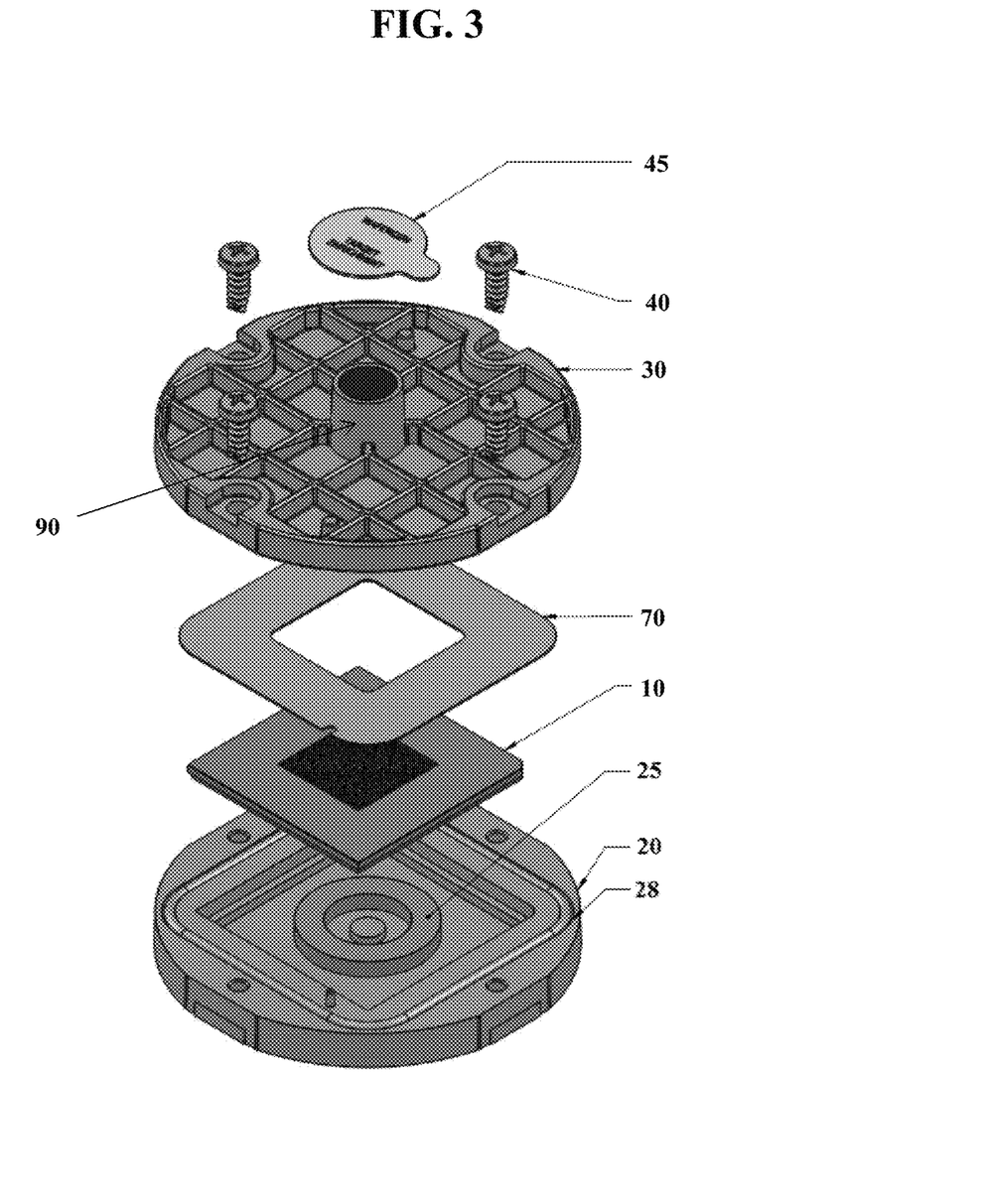
FIG. 3 shows an exemplary embodiment of an extraction fixture which contains a paper gasket (70).

In certain embodiments, the extraction fixtures of the present invention employ a paper gasket (e.g., between the nanowell chip and fixture top plate). An exemplary embodiment of an extraction fixture is shown in FIG. 3. FIG. 3 shows a paper gasket (70) between the nanowell chip (10) and the fixture top plate (30). Also shown in FIG. 3 is a sample cup (90) in fixture top plate (30) where sample could be introduced. A protective label (45) is shown which can cover the sample cup (90). Four screws (40) (which could be any type of attachment component) are shown in fixture top plate (30) for attaching all of the components together (e.g., for anchoring in the holes shown in extraction fixture base (20). Also shown in extraction fixture base (20) is gasket track (28) shown with a rubber gasket in place.

The paper gasket, in certain embodiments, is used to prevent or slow the leakage of sample material added to the nanowell chip in the extraction fixtures of the present invention (e.g., when liquid sample is injected into the extraction fixture via the sample cup). Any type of suitable paper may be employed for the paper gaskets. Preferably the paper gaskets are composed of a type of paper which is useful in corralling the liquid flow front and absorbing the excess liquid, but not too quickly (e.g., papers that absorb the liquid sample too quickly are not preferred as this could result in a low fill weight into the nanowell chip). In certain embodiments, the type of paper employed is inkjet paper, such as KODAK inkjet paper (e.g., 30-70 pound inkjet paper, or about 44 pound inkjet paper, or 80 pound inkjet paper). In certain embodiments, the paper employed is filter paper, blotting paper, shim paper, or chromatography paper. In certain embodiments, the paper employed is 44 pound matte inkjet paper (e.g., from KODAK). In certain embodiments, the paper gasket is between 0.005 and 0.009 inches in thickness. In some embodiments, the paper employed is uncoated commodity grade paper, uncoated surface treated paper, or a coated paper (e.g., as types of inkjet paper). In particular embodiments, the paper is acid free art paper (e.g., about 60 . . . 70 . . . 80 pound acid free art paper).

In certain embodiments, the paper employed for the paper gaskets is a blotting, shim, or chromatography type paper. Examples of such papers include shim/blotter paper, standard grades, wet strengthened, hardened low ash grades, and hardened ashless grades, which are found in Tables 1-5 below:

TABLE 1

| Paper candidates for shim/blotter | | | | | |
|---|---|---|---|---|---|
| Vendor | Type | Vendor PN | thickness | Flow | Herzberg Absorbency |
| Whatman | Blotter | 703 | 0.38 | 250 s | 626 sec./7.5 cm rise |
| Whatman | Blotter | 3 MM | 0.34 | | 130 mm/30 min |
| Whatman | Blotter | Grade 2 Chr | 0.18 | | 115 mm/30 min |
| Whatman | Filter | 542 | 0.15 | 2510 s | — |
| Whatman | | 114 | 0.19 | 38 s | |

TABLE 2

| Standard Grade | | Particle retention | Filtration speed (approx.) | Air flow | Typical thickness | Basis weight |
|---|---|---|---|---|---|---|
| Grade | Description | in liquid (μm) | herzberg (s) | (s/100 ml/in²) | (μm) | (g/m²) |
| 1 | Medium flow | 11* | 150 | 10.5 | 180 | 88 |
| 2 | Medium flow | 8* | 240 | 21 | 190 | 103 |
| 3 | Medium flow, thick | 6* | 325 | 26 | 390 | 187 |
| 4 | Very fast | 20 to 25* | 37 | 3.7 | 205 | 96 |
| 5 | Slow | 2.5* | 1420 | 94 | 200 | 98 |
| 6 | Medium to slow | 3* | 715 | 35 | 180 | 105 |
| 591 | Medium fast, thick | 7 to 12† | 45 | 5.9 | 350 | 161 |
| 595 | Medium fast, thin | 4 to 7† | 80 | — | 150 | 68 |

TABLE 2-continued

| Standard Grade | | Particle retention | Filtration speed (approx.) | Air flow | Typical thickness | Basis weight |
|---|---|---|---|---|---|---|
| Grade | Description | in liquid (μm) | herzberg (s) | (s/100 ml/in²) | (μm) | (g/m²) |
| 597 | Medium fast | 4 to 7† | 140 | — | 180 | 85 |
| 598 | Medium fast, thick | 8 to 10† | 50 | — | 320 | 140 |
| 602 h | Slow, dense | <2† | 375 | — | 160 | 84 |

TABLE 3

| Wet strengthened | | Particle retention | Filtration speed (approx.) | Air flow | Typical thickness | Basis weight |
|---|---|---|---|---|---|---|
| Grade | Description | in liquid (μm) | herzberg (s) | (s/100 ml/in²) | (μm) | (g/m²) |
| 91 | Creped | 10* | 70 | 6.2 | 205 | 71 |
| 93 | Medium | 10* | 80 | 7 | 145 | 67 |
| 113 | Fast, creped | 30* | 28 | 1.3 | 420 | 125 |
| 114 | Fast, smooth | 25* | 38 | 5.3 | 190 | 77 |
| 588 | Fast | — | — | — | 205 | 80 |
| 1573 | Fast, smooth | 12 to 25† | 25 | — | 170 | 88 |
| 1575 | Slow | <2† | 700 | — | 140 | 92 |

TABLE 4

| Hardened Low Ash Grades | | Particle retention | Filtration speed | Ash content* | Typical thickness | Basis weight |
|---|---|---|---|---|---|---|
| Grade | Description | in liquid (μm) | herzberg (s) | (%) | (μm) | (g/m²) |
| 40 | Medium flow | 8† | 340 | 0.007 | 210 | 95 |
| 41 | Fast | 20† | 54 | 0.007 | 220 | 85 |
| 42 | Slow | 2.5† | 1870 | 0.007 | 200 | 100 |
| 43 | Medium to fast | 16† | 155 | 0.007 | 220 | 95 |
| 44 | Slow to medium | 3† | 995 | 0.007 | 180 | 80 |
| 589/1 | Fast | 12-25‡ | 25 | 0.01 | 190 | 80 |
| 589/2 | Medium fast | 4-12‡ | 70 | 0.01 | 180 | 85 |
| 589/3 | Slow | <2‡ | 375 | 0.01 | 160 | 84 |

TABLE 5

| Hardened Ashless Grades | | Particle Retention | Filtration Speed | Ash Content* | Typical Thickness | Basis Weight |
|---|---|---|---|---|---|---|
| Grade | Description | in Liquid (μm) | Herzberg (s) | (%) | (μm) | (g/m²) |
| 50 | Slow | 2.7† | 2685 | 0.015 | 115 | 97 |
| 52 | Medium | 7† | 235 | 0.015 | 175 | 101 |
| 54 | Very fast | 2.2† | 39 | 0.015 | 185 | 92 |

Figure 4:
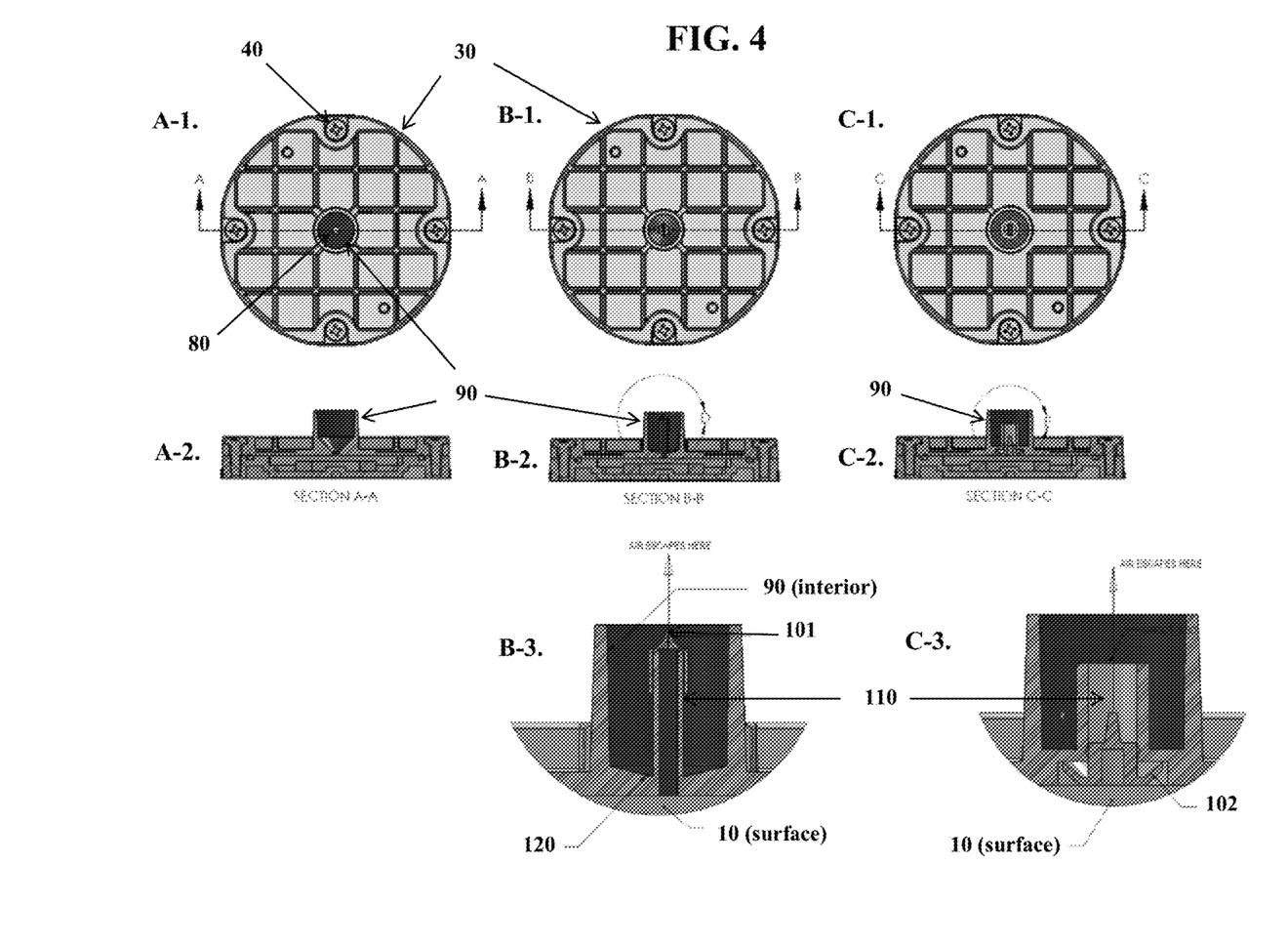

In certain embodiments, the nanowell chips are loaded with sample when the nanowell chips are already present inside the extraction fixture. Such loading can be accomplished, for example, with bulk fill fixtures that form part of the fixture top plate (e.g., and which allow liquid to be transmitted through the fixture top plate). FIGS. 3 and 4 show part of the bulk fill fixture called a sample cup (90), which extends trough the fixture top plate (30) such that sample can be introduced into the nanowell chip when it is already inside the extraction fixture.

FIG. 4 shows various exemplary embodiments of bulk fill fixtures in the fixture top plates. FIG. 4A-1 shows a top view of a fixture top plate (30) with a sample cup (90) formed in the center thereof with a septum (80) in the center of the sample cup to allow needle injection of sample into the sample cup (e.g., needle injection of sample when the extraction fixture is on top of a vacuum fill station that draws the sample down into the nanowell chip below). FIG. 4A-2 shows a side view of the sample cup (90) through section A-A of FIG. 4A-1. FIG. 4B-1 shows a top view of a fixture top plate (30) with a sample cup (90) formed in the center thereof, while FIG. 4B-2 shows a side view of FIG. 4B-1 through section B-B. In such embodiments, a sample may be pre-loaded into the bulk fill fixture before the extraction fixture is placed in the fill station (e.g., which can apply a vacuum). FIG. 4B-3 shows a blow up of the bulk fill fixture in FIG. 4B-2, showing a spigot (110) and a duckbill valve (101) on top of the spigot, which allows air out when a vacuum is applied (or released) drawing the sample down (part 120 shows an exemplary liquid front and how the liquid can flow onto the chip when a vacuum is released, or applied) into the nanowell chip (10) thereby preventing bubbling of liquid in the sample cup. FIG. 4C-1 shows a top view of a fixture plate (30) with a sample cup (90) formed in the center thereof, which FIG. 4C-2 shows a side view of FIG. 4C-1 through section C-C. In such embodiments, a sample may be pre-loaded into the bulk fill fixture before the extraction fixture is placed in the fill station (e.g., which can apply or release a vacuum). FIG. 4C-3 shows a blow up of the bulk fill fixture in FIG. 4C-2, showing a spigot (110) and a combo valve (102) which vents through a duckbill valve while allowing liquid to flow in thru the umbrella portion.

The present invention is not limited by the type of miniature valve that is employed. Exemplary miniature valves (e.g., from MINI-VALVE corporation) include, but are not limited to: duckbill valves, umbrella valves, belleville valves, duckbill-umbrella combination valves, x-fragm valves, minivalveballs, cross-slit valves, and dome valves.

The present invention is not limited by the shape, size, or composition of the extraction fixture. Any extraction fixture that is able to collect (and hold or transmit to another component) liquid forced out of nanowells (from the entire chip or a selected portion thereof) is useful in the present invention. In certain embodiments, the extraction fixtures have a general conical shape (e.g., as shown in FIG. 1) that fits over at least a portion of a nanowell chip. In other embodiments, the extraction fixture is flat or partially flat, but has the ability to collect liquid forced out of nanowells. In certain embodiments, the extraction fixtures have attachments components that allow attachment or mating to a nanowell chip. In particular embodiments, the extraction fixtures have a portion that concentrates fluid into a smaller region such that it can be easily removed (e.g., by a pipette). In some embodiments, the collections fixtures comprise a material selected from glass, silicon, metal, or other suitable material. In additional embodiments, the size of the extraction fixtures is determine by the size of the nanochip to which it is attached and/or the size of the device into which the chip-extraction fixture assembly is inserted (e.g., the size of the extraction fixture is such that the assembly that is formed can fit onto an arm of a centrifuge).

The present invention is not limited by the type of chips employed. In general, such chips have a plurality of wells that contain, or are dimensioned to contain, liquid that is trapped in the wells such that gravity alone cannot make the liquid flow out of the wells (e.g., surface tension-restrained liquid is in the wells). Exemplary chips are provided in U.S. Pat. Nos. 8,252,581; 7,833,709; and 7,547,556, all of which are herein incorporated by reference in their entireties including, for example, for the teaching of chips, wells, thermocycling conditions, and associated reagents used therein). Other exemplary chips include the OPENARRAY plates used in the QUANTSTUDIO real-time PCR system (Applied Biosystems).

The overall size of a chip of the invention may vary and it can range, for example, from a few microns to a few centimeters in thickness, and from a few millimeters to 50 centimeters in width or length. Typically, the size of the entire chip ranges from about 10 mm to about 200 mm in width and/or length, and about 1 mm to about 10 mm in thickness. In some embodiments, the chip is about 40 mm in width by 40 mm in length by 3 mm in thickness.

The chip can also be, for example, a set of smaller chips. For example, the chip can comprise two to nine smaller chips (e.g., two . . . six . . . or nine arrays of addressable units) with a thermal buffer between each of the smaller chips. A chip that is a set of smaller chips is also referred to herein as a plate. In an embodiment of this example, each of the smaller chips corresponds to a different predetermined temperature to which the array of units in the overall chip are addressed.

The total number of wells (e.g., nanowells) on the chip may vary depending on the particular application in which the subject chips are to be employed. The density of the wells on the chip surface may vary depending on the particular application. The density of wells, and the size and volume of wells, may vary depending on the desired application and such factors as, for example, the species of the organism for which the methods of this invention are to be employed.

The present invention is not limited by the number of wells in the nanochips. A large number of wells may be incorporated into a chip. In various embodiments, the total number of wells on the chip is from about 100 to about 200,000, or from about 5000 to about 10,000. In other embodiments the chip comprises smaller chips, each of which comprises about 5,000 to about 20,000 wells. For example, a square chip may comprise 125 by 125 nanowells, with a diameter of 0.1 mm.

The wells (e.g., nanowells) in the chips may be fabricated in any convenient size, shape or volume. The well may be about 100 µm to about 1 mm in length, about 100 µm to about 1 mm in width, and about 100 µm to about 1 mm in depth. In various embodiments, each nanowell has an aspect ratio (ratio of depth to width) of from about 1 to about 4. In one embodiment, each nanowell has an aspect ratio of about 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from about 0.1 nl to about 1 ul. The nanowell typically has a volume of less than 1 ul, preferably less than 500 nl. The volume may be less than 200 nl, or less than 100 nl. In an embodiment, the volume of the nanowell is about 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

A well of high inner surface to volume ratio may be coated with materials to reduce the possibility that the reactants contained therein may interact with the inner surfaces of the well if this is desired. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, AQUASIL, and SURFASIL. Additional suitable coating materials are blocking agents such as amino acids, or polymers including but not limited to polyvinylpyrrolidone, polyadenylic acid and polymaleimide. Certain coating materials can be cross-linked to the surface via heating, radiation, and by chemical reactions. Those skilled in the art will know of other suitable means for coating a nanowell of a chip, or will be able to ascertain such, without undue experimentation.

In some embodiments, an individual unit of the chip comprises a nanowell for receiving and confining a sample, said well being sealed when filled with the sample. The individual wells within the array can be separated from each other by a physical barrier resistant to the passage of liquids. A well can be open at the top, but is generally physically isolated from other wells to restrict passage of liquids. Accordingly, a well has at least one cavity suitable for receiving and confining reaction sample. In order to isolate one well from the environment to restrict the passage of liquids, the well can be sealed. In certain embodiments, a method of sealing a nanowell is depositing mineral oil on top of the sample within the well to confine the sample. The mineral oil can be nano-dispensed. A well can be sealed by any suitable method.

In many applications, sealing wells is desirable to prevent evaporation of liquids and thus maintains the preferred reaction concentrations throughout the thermal cycling. Accordingly, a technique for sealing an array of nanowells can be employed. Such seals can be permanent or removable. A useful sealing technique takes several factors into consideration. First, the method should generally be amenable to high throughout processing of a large quantity of wells. Second, the method should generally permit selective sealing of individual nanowells. As such, the method can yield chips comprising open wells interspersed among sealed nanowells in any desired pattern or format. An open and/or unfilled well can not only allow passive dissipation of heat, but also can reduce heat transfer between the neighboring nanowells. An alternative method of sealing results in an array of wells containing at least one open well. The method can include the steps of (a) applying a radiation-curable adhesive along peripheral dimensions defining the open surface of the at least one open well; (b) placing a cover to encompass the peripheral dimensions that define the open surface of the at least one open well that is to be sealed; and (c) exposing the array to a radiation beam to effect the sealing.

An exemplary chip may have a thickness of about 0.625 mm, with a well have having dimensions of about 0.25 mm (250 um) in length and width. The nanowell depth can be about 0.525 mm (525 um), leaving about 0.1 mm of the chip beneath a given well. A nanowell opening can include any shape, such as round, square, rectangle or any other desired geometric shape. By way of example, a nanowell can include a diameter or width of between about 100 um and about 1 mm, a pitch or length of between about 150 um and about 1 mm and a depth of between about 10 um to about 1 mm. The cavity of each well make take a variety of configurations. For instance, the cavity within a nanowell may be divided by linear or curved walls to form separate but adjacent compartments.

The wells (e.g., nanowells) of the chip may be formed using, for example, commonly known photolithography techniques. The nanowells may be formed using a wet KOH etching technique or an anisotropic dry etching technique.

A well of high inner surface to volume ratio may be coated with materials to reduce the possibility that the reactants contained therein may interact with the inner surfaces of the nanowells. A chip can also be made of resistive heating material. Non-limiting examples of materials include metal plates such as aluminum and stainless steel substrates such as SS-316. Where the substrate used is a metal, it is usually preferable to coat the surface with an insulating layer to prevent corrosion and/or electrolysis of the substrate during operation with fluid samples. Coating is usually not necessary in the case or non-metal heating material. A variety of protective coatings are available, including those made of, for example, $SiO_2$, $Si_3N_4$, and Teflon.

The surface of a well (e.g., nanowell) of a chip can further be altered to create adsorption sites for reaction reagents. These sites may comprise linker moieties for attachment of biological or chemical compound such as a simple or complex organic or inorganic molecules, a peptide, a protein (for example antibody) or a polynucleotide. One skilled in the art will appreciate that there are many ways of creating adsorption sites to immobilize chemical or biological reactants. For instance, a wealth of techniques are available for directly immobilizing nucleic acids and amino acids on a chip, anchoring them to a linker moiety, or tethering them to an immobilized moiety, via either covalent or non-covalent bonds (see, for example, Methods Mol. Biol. Vol. 20 (1993), Beier et al., Nucleic Acids Res. 27:1970-1-977 (1999), Joos et al., Anal. Chem. 247:96-101 (1997), Guschin et al., Anal. Biochem. 250:203-211 (1997); all of which are herein incorporated by reference). The surface of the nanowell can be plasma etched to allow for immobilization of a probe or primer.

As used herein, the term "chemical reaction" refers to any process involving a change in chemical properties of a substance. Such process, includes a vast diversity of reactions involving biological molecules such as proteins, glycoproteins, nucleic acids, lipids, and inorganic chemicals, or any combinations thereof. The chips have a wide variety of uses in chemical and biological applications. The chemical reaction may involve interactions between nucleic acid molecules, between proteins, between nucleic acid and protein, between protein and small molecules. Where the process is catalyzed by an enzyme, it is also referred to as "enzymatic reaction."

The chips are generally useful in conducting enzymatic reactions. Representative enzymatic reactions that may be accomplished in the wells of a chip include but are not limited to nucleic acid amplification, such as quantitative polymerase chain reaction (qPCR), nucleic acid sequencing, reverse transcription, and nucleic acid ligation. In an embodiment, a nucleic acid amplification reaction run on a chip is a real-time polymerase chain reaction. In another embodiment, the nucleic acid amplification reaction is a reverse-transcription coupled polymerase chain reaction.

As used herein, "nucleic acid amplification" refers to an enzymatic reaction in which the target nucleic acid is increased in copy number. Such increase may occur in a linear or in an exponential manner. Amplification may be carried out by natural or recombinant DNA polymerases such as, for example, Taq polymerase, Pfu polymerase, T7 DNA polymerase, Klenow fragment of E. coli DNA polymerase, and/or RNA polymerases such as reverse transcriptase.

In general, the purpose of a polymerase chain reaction (PCR) is to manufacture a large volume of DNA which is identical to an initially supplied small volume of target or seed DNA. The reaction involves copying the strands of the DNA and then using the copies to generate other copies in subsequent cycles. Each cycle will approximately double the amount of DNA present thereby resulting in a geometric progression in the volume of copies of the target DNA strands present in the reaction mixture. General procedures for PCR are taught in U.S. Pat. No. 4,683,195 (Mullis) and U.S. Pat. No. 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids. A typical conventional PCR thermal cycling protocol comprises 30 cycles of (a) denaturation at a range of 90 degrees C. to 95 degrees C., (b) annealing at a temperature ranging from 50 degrees C. to 68 degrees C., and (c) extension at 68 degrees C. to 75 degrees C.

The chips can be employed in reverse transcription PCR reaction (RT-PCR). RT-PCR is another variation of the conventional PCR, in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (for example, 30-45 degrees C.) for a sufficient amount of time (for example, 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample.

Methods of "quantitative" amplification of nucleic acids are well known to those of skill in the art. For example, quantitative PCR (qPCR) can involve simultaneously co-amplifying a known quantity of a control sequence using the same primers. This provides an internal standard that may be used to calibrate the PCR reaction. Other ways of performing qPCR are available in the art. Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

Reagents contained within the liquid in the nanowells of a chip depend on the reaction that is to be run. In an embodiment, at least one of the wells of the array of addressable units contains a reagent for conducting the nucleic acid amplification reaction. Reagents can be reagents for immunoassays, nucleic acid detection assays including but not limited to nucleic acid amplification. Reagents can be in a dry state or a liquid state in a unit of the chip. In an embodiment, at least one of the wells in the chip capable of carrying out a nucleic acid amplification reaction contains at least one of the following: a probe, a polymerase, and dNTPs. In another embodiment, the nanowells of a chip contain a solution comprising a probe, a primer and a polymerase. In various embodiments, each chamber comprises (1) a primer for a polynucleotide target within said standard genome, and (2) a probe associated with said primer which emits a concentration dependent signal if the primer binds with said target. In various embodiments, each well comprises a primer for a polynucleotide target within a genome, and a probe associated with the primer which emits a concentration dependent signal if the primer binds with the target. In another embodiment, at least one well of the chip contains a solution that comprises a forward PCR primer, a reverse PCR primer, and at least one FAM labeled MGB quenched PCR probe. In an embodiment, primer pairs are dispensed into a well and then dried, such as by freezing. The user can then selectively dispense, such as nano-dispense, the sample, probe and/or polymerase.

In other embodiments of the invention, the wells may contain any of the above solutions in a dried form. In this embodiment, this dried form may be coated to the wells or be directed to the bottom of the well. The user can add a mixture of water and the sample to each of the wells before analysis. In this embodiment, the chip comprising the dried down reaction mixture may be sealed with a liner, stored or shipped to another location (e.g., in combination with the extraction fixtures described herein). The liner is releasable in one piece without damaging the adhesive uniformity. The liner is visibly different than the cover to aid in identification and for ease of handling. The material of the liner is chosen to minimize static charge generation upon release from the adhesive. When the user is ready to use the chip, the seal is broken and the liner is removed and the sample is added to the units of the chip. In many applications, sealing the nanowells is desirable to prevent evaporation of liquids and thus maintains the preferred reaction concentrations throughout the thermal cycling.

The chip may be used for genotyping, gene expression, or other DNA assays preformed by PCR. Assays performed in the plate are not limited to DNA assays such as TAQMAN, TAQMAN Gold, SYBR gold, and SYBR green but also include other assays such as receptor binding, enzyme, and other high throughput screening assays. In some embodiments, a ROX labeled probe is used as an internal standard.

The invention also provides a method for performing a PCR analysis using a chip comprising a plurality of preloaded nanowells, the method comprising: placing a sample into the nanowells to create a reaction mixture; sealing the nanowells of the chip with mineral oil or another sealing mechanism; placing the chip into a thermal cycling system; cycling the system; analyzing results; and extracting the reagents from the nanowells into a capture fixture.

The chips may be composed of any suitable substrate. The substrate is often a good thermal conductor. A good thermal conductor generally has a thermal conductivity value higher than 1 W/m$^{-1}$K$^{-1}$, preferably higher than 100 W/m$^{-1}$ K$^{-1}$, more preferably higher than 140 W/m$^{-1}$K$^{-1}$. Whereas the material's thermal conductivity may be 250 W/m$^{-1}$K$^{-1}$ or higher, it usually does not exceed 500 W/m$^{-1}$K$^{-1}$. In certain embodiments, the substrate is relatively inert and chemically stable. Such substrates generally exhibit a low level of propensity to react with the reaction samples employed in the intended application. In some embodiments, the material is selected based upon the ability or feasibility to integrate thermal control elements onto or adjacent to them. Exemplary materials include, but are not limited to, metalloids or semiconductors, such as silicon, silicates, silicon nitride, silicon dioxide, gallium phosphide, gallium arsenide, or any combinations thereof. Other materials include glass, ceramics (including crystalline and non-crystalline silicate, and non-silicate-based ceramics), metals or alloys, composite polymers that contain dopants (for example, aluminum oxide to increase thermal conductivity), or any of a range of plastics and organic polymeric materials available in the art. In one embodiment, the nanowells are fabricated in such substrates including Al or SS-316 as well as similar others.

In certain embodiments, the chips are fabricated using a thermally conductive polymer. For example, the chips can be fabricated using polycarbonate, polypropylene, or any other conductive polymer known to those with skill in the art. The chips can be fabricated by any suitable method. Examples of method of making a chip include, but are not limited to, micro drilling, electric discharge method, hot embossing, and hot embossing with a tool made from which uses water as light guide. Alternatively, chips can be fabricated using techniques well established in the Integrated Circuit (IC) and Micro-Electro-Mechanical System (MEMS) industries. The fabrication process typically proceeds with selecting a chip substrate, followed by using appropriate IC processing methods and/or MEMS micromachining techniques to construct and integrate various components. Fabrication of chips can be performed according to standard techniques of IC-processing and/or MEMS micromachining. The chips can be fabricated as multi-layer structures. The process generally proceeds with constructing the bottom layer. Then a combination of techniques including but not limited to photolithography, chemical vapor or physical vapor deposition, dry or wet etching are employed to build structures located above or embedded therein. Vapor deposition, for example, enables fabrication of an extremely thin and uniform coating onto other materials, whereas etching allows for mass production of larger chip structures. Other useful techniques such as ion implantation, plasma ashing, bonding, and electroplating can also be employed to improve the surface properties of the chips or to integrate various components of the chips.

In certain embodiments, the devices, articles, and assemblies are part of a system, such as an automated sample processing system (e.g., that has central computer control). In particular embodiments, the system provides at least partial automation that includes sample preparation, reaction in a chip (e.g., PCR reaction in the nanowells of a chip), analysis of the reaction (e.g., optical real-time amplicon accumulation), data analysis/storage/display, and collection of restrained liquid from nanowells of the chip (e.g., using the extraction fixtures described herein). In particular embodiments, the system further comprises further manipulation of the collected liquid from the nanowells.

The present invention also provides methods of reducing the dynamic range of amplicons produced on a nanowell chip (e.g., chips that come pre-loaded with primer pairs in the wells), such as Wafergen'S SMARTCHIP. A large difference in the number of amplicons produced in certain wells compared to other wells can create a large dynamic range (a large difference in amount of amplicons produced in certain wells versus others). Such large differences can create a large discrepancy in depth of coverage when the amplicons are sequenced. One reason that there can be a difference in amplicon production between wells relates to primer design and subsequent efficiency in a PCR reaction. With nanowell chips (e.g., with wells pre-loaded with PCR primers) often, within the amplicons of interest, there is a range of amplicon amplification that can lead to a large range in sequencing coverage when the amplicons are sequenced. This difference in coverage may, for example, be up to 50 fold or more. For instance, with 1000 sequenced amplicons, it would not be atypical to have a sequencing coverage range from 30× to 1500×, or, a 50-fold spread.

Exemplary methods to reduce the dynamic range of coverage in nanowell chips such that amplicons produced for a given target on the chip are at least partially normalized are as follows. Such methods may be used singly or combined in any and all combinations:

i) In particular embodiments, if certain wells are found to be low expressers on a particular chip, the chip configuration could be modified to use more of the available wells for the low expressing amplicons to bring the total amount up relative to other wells. For example, if the span in coverage is 30× to 1500×, and the 30× wells are then run in triplicate, the expected coverage range would then be 90× to 1500×, or only a 17× span.

ii) In another embodiment, high expressing amplicons could be multiplexed in order to reduce their production. For example, for multiplexing of small numbers of amplicons, for example two-plexes to four-plexes, primer designs are made simpler than single tube assays where many of hundreds of primers are combined, and the chance for deleterious interactions is greater.

iii) In some embodiments, one approach is based on primer titration and dilution of primers for the high amplicon reactions and/or conversely increasing primer concentrations for the low amplicon reactions.

iv). Another method for reducing the dynamic range with amplification of amplicons relates to using a master mix designed for GC rich targets. One issue with certain targets is that GC rich regions typically produce low amounts of amplicons. For example, the master mix could include betaine or other reagents that allow for increased PCR amplification of GC rich regions.

v) In certain embodiments, targets that generate high amplicon levels with standard primers could be switched to primers that are less efficient for that target such that the level of amplicons produced during PCR is reduced.

vi) In particular embodiments, the thermalcycling temperature of particular wells can be altered such that a lower amount (or higher amount) of amplicon is produced in a given well.

vii) In some embodiments, the depth, width, and/or overall volume of wells is adjusted to compensate for high or low producing amplicons. For example, deeper wells may be employed for low expressing amplicons, while shallower wells may be used for high expressing amplicons.

As mentioned above, in certain embodiments, multiplexing is employed to reduce the concentration of the high expressing amplicons. The following simplified example can be employed to determine if such multiplexing would be helpful with a particular set of primers. One chooses four primers with roughly equivalent CTs on human genomic DNA (e.g. four primers from BCH, "A", "B", "C", "D"). These primer are dispensed in the wells of a 384 well plate or nanowell chip in the following seven configurations: A, B, C, D, A+B, A+B+C, and A+B+C+D. All primers are dispensed at nominal concentrations and thermocycled (e.g., on an LC480). The DNA concentrations of amplicons are then be measured in each well (e.g., using a Nanodrop). If all the wells have roughly the same concentration of DNA, then multiplexing to attenuate the high expressing assays should be helpful. If the DNA concentration scales with the number of primers in the well, then multiplexing probably won't help.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising:
    a) a chip, wherein said chip comprises a substrate and a plurality of open wells formed in said substrate, wherein said plurality of fluidically isolated open wells contain restrained liquid, and
    b) an extraction fixture dimensioned to be attached to said chip to form an assembly, wherein said extraction fixture comprises:
        a base; and
        a conical section in said base dimensioned to receive said restrained liquid from at least a portion of said plurality of open wells when said restrained liquid is forced out of said plurality of open wells;
    wherein said extraction fixture is mated to said chip such that at least a portion of said plurality of open wells of said chip are facing said conical section of said extraction fixture.

2. The system of claim 1, wherein said extraction fixture further comprises a fluid holding component at a bottom of said conical portion.

3. The system of claim 1, wherein said extraction fixture is attached to a liquid collection holder.

4. The system of claim 3, wherein said liquid collection holder is in liquid receiving relationship with said extraction fixture.

5. The system of claim 4, wherein said liquid collection holder is a tube.

6. The system of claim 1, further comprising a base holding component, wherein said base holding component is dimensioned to hold said extraction fixture.

7. The system of claim 6, wherein said base holding component comprises a liquid collection holder mounted in said base holding component.

8. The system of claim 7, wherein said liquid collection holder comprises a tube.

9. The system of claim 6, wherein said base holding component fits onto an arm of a centrifuge.

10. The system of claim 6, wherein said chip and said extraction fixture is placed in said base holding component such that said plurality of open wells of said chip are facing said extraction fixture and base holding component.

11. The system of claim 1, wherein said extraction fixture is made of a material selected from the group consisting of: glass, silicon, and metal, or any combination thereof.

12. The system of claim 1, further comprising a centrifuge.

13. The system of claim 1, wherein said chip comprises at least 1000 wells.

14. The system of claim 1, wherein said open wells have a volume from 0.1 nL to 1 µL.

15. The system according to claim 1, further comprising an extraction fixture top plate.

* * * * *